(12) United States Patent  (10) Patent No.: US 8,034,099 B2
Pellegrini  (45) Date of Patent: Oct. 11, 2011

(54) STENT PROSTHESIS HAVING SELECT FLARED CROWNS

(75) Inventor: Gianfranco Pellegrini, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 743 days.

(21) Appl. No.: 12/057,032

(22) Filed: Mar. 27, 2008

(65) Prior Publication Data

US 2009/0248139 A1  Oct. 1, 2009

(51) Int. Cl.
*A61F 2/06* (2006.01)

(52) U.S. Cl. ...... 623/1.15; 623/1.1; 623/1.16; 623/1.17; 623/1.3; 623/1.31

(58) Field of Classification Search .......... 623/1.1–1.22, 623/1.36–1.37, 11.11, 23.64, 23.7, 900, 1.3, 623/1.31
See application file for complete search history.

(56) References Cited

U.S. PATENT DOCUMENTS

| | | | |
|---|---|---|---|
| 5,458,639 A | 10/1995 | Tsukashima et al. | |
| 5,957,949 A | 9/1999 | Leonhardt et al. | |
| 6,056,776 A | 5/2000 | Lau et al. | |
| 6,066,169 A | 5/2000 | McGuinness | |
| 6,500,147 B2 | 12/2002 | Omaleki et al. | |
| 6,554,795 B2 | 4/2003 | Bagaoisan et al. | |
| 6,736,827 B1 | 5/2004 | McAndrew et al. | |
| 6,773,455 B2 * | 8/2004 | Allen et al. | 623/1.15 |
| 6,805,705 B2 * | 10/2004 | Hong et al. | 623/1.15 |
| 6,846,323 B2 | 1/2005 | Yip et al. | |
| 2002/0123791 A1 | 9/2002 | Harrison | |
| 2009/0216313 A1 * | 8/2009 | Straubinger et al. | 623/1.17 |

* cited by examiner

*Primary Examiner* — Corrine M McDermott
*Assistant Examiner* — Todd J Scherbel

(57) ABSTRACT

A generally tubular, cylindrical stent prosthesis has an unexpanded delivery configuration and an expanded configuration for contacting the vessel wall. The stent prosthesis has a plurality of adjacent stent struts, each stent strut having a wavelike or sinusoidal pattern of straight segments and crowns. A Y-shaped member is attached to one or more crowns to cause the crowns to flare outwardly at an angle from the cylindrical stent body when the stent is expanded. Upon expansion of the stent, the crown(s) having Y-shaped members attached thereto are angled with respect to the longitudinal axis and radially flare from the cylindrical stent body. The flared crowns anchor the stent within the vessel by protruding into the vessel wall and/or seating the stent within an ostium.

11 Claims, 11 Drawing Sheets

STENT PROSTHESIS HAVING SELECT FLARED CROWNS

FIELD OF THE INVENTION

The present invention is directed to a stent prosthesis for use in a body lumen. More particularly, the present invention is directed to a stent prosthesis design to induce flaring of select stent crowns.

BACKGROUND OF THE INVENTION

Heart disease, specifically coronary artery disease, is a major cause of death, disability, and healthcare expense in the United States and other industrialized countries. A number of methods and devices for treating coronary heart disease have been developed, some of which are specifically designed to treat the complications resulting from atherosclerosis and other forms of coronary arterial narrowing.

One method for treating such conditions is percutaneous transluminal coronary angioplasty (PTCA). Generally, PTCA is a procedure that involves passing a balloon catheter over a guidewire to a stenosis with the aid of a guide catheter. The stenosis may be the result of a lesion such as a plaque or thrombus. The guidewire extends from a remote incision to the site of the stenosis, and typically across the lesion. The balloon catheter is passed over the guidewire, and ultimately positioned across the lesion. Once the balloon catheter is appropriately positioned across the lesion, e.g., under fluoroscopic guidance, the balloon is inflated to break-up the plaque of the stenosis to thereby increase the vessel cross-section. The balloon is then deflated and withdrawn over the guidewire into the guide catheter to be removed from the body of the patient. In many cases, a stent or other prosthesis must be implanted to provide permanent support for the vessel. Stent prostheses are known for implantation within body lumens to provide artificial radial support to the wall tissue, which forms the various lumens within the body, and often more specifically, for implantation within the blood vessels of the body. Stents are typically constructed of a metal or polymer and are generally a hollow cylindrical shape. When such a device is to be implanted, a balloon catheter, typically carrying a stent on its balloon, is deployed to the site of the stenosis. The balloon and accompanying stent are positioned at the location of the stenosis, and the balloon is inflated to circumferentially expand and thereby implant the stent. Thereafter, the balloon is deflated and the catheter and the guidewire are withdrawn from the patient.

Recently, flexible stented valve prostheses and various delivery devices have been developed so that replacement valves can be delivered transvenously using a catheter-based delivery system. These stented valves may include a collapsible valve attached to the interior of a tubular frame or stent. The stented valves may also have a tubular portion or "stent graft" that can be attached to the interior or exterior of the stent to provide a generally tubular internal passage for the flow of blood when the leaflets are open. The graft can be separate from the valve and it can be made from any suitable biocompatible material including, but not limited to, fabric, a homograft, porcine vessels, bovine vessels, and equine vessels. The stent portion of the device can be reduced in diameter, mounted on a catheter, and advanced through the circulatory system of the patient. The stent portion can be either self-expanding or balloon expandable. In either case, the stented valve can be positioned at the delivery site, where the stent portion is expanded against the wall of a previously implanted prostheses or a native vessel to hold the valve firmly in place. The valve survives the compression and subsequent expansion in fully working form. One embodiment of a stented valve is disclosed in U.S. Pat. No. 5,957,949 titled "Percutaneous Placement Valve Stent" to Leonhardt et al., the contents of which are incorporated by reference herein in its entirety. Although the valve may later require replacement, the patient may receive multiple replacement valves using the minimally invasive catheter method rather than requiring further invasive surgery.

Stents prostheses, including those used in percutaneous heart valve applications, often do not have vessel fixation properties other than providing a coaxial interference fit into the target vessel or location. It is thus an object of the present invention to improve stent retention within a body lumen.

BRIEF SUMMARY OF THE INVENTION

Embodiments of the present invention relate to a stent for use within a body lumen, the stent including a stent strut having a sinusoidal pattern of straight segments and crowns. All of the crowns of the stent strut are approximately parallel with a longitudinal axis of the stent when the stent is in an unexpanded configuration for delivery within the body lumen. The stent also includes a Y-shaped member attached to at least one crown of the stent strut such that the Y-shaped member is substantially centered within the at least one crown and the straight segments that extend from the at least one crown. When the stent is in an expanded configuration for contacting a vessel wall of the body lumen the at least one crown having the Y-shaped member attached thereto radially flares outward from an outer surface of the stent such that the at least one crown is at an acute angle with respect to the longitudinal axis of the stent.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments of the present invention relate to a generally tubular, cylindrical stent prosthesis in which select crowns of a stent strut flare radially outward at an angle from the cylindrical stent body upon expansion of the stent. A Y-shaped member is attached to one or more crown(s) to induce crown flaring. When the stent is in the unexpanded delivery configuration, all of the stent crowns are approximately parallel with a longitudinal axis of the stent. Upon expansion of the stent, the crown(s) having Y-shaped members attached thereto are angled with respect to the longitudinal axis and radially flare from the cylindrical stent body. The flared crowns may operate to anchor or retain the stent within the vessel by protruding into the vessel wall and/or seating the stent within an ostium of a body lumen. The flared crowns may additionally or alternatively operate to contain or "jail" plaque, to pry open an occlusion, to create an ostia, and/or to ease the crossing of another device. In one embodiment, the stent prosthesis is balloon expandable. Further details and description of the embodiments of the present invention are provided below with reference to FIGS. 1-13.

Figure 1:
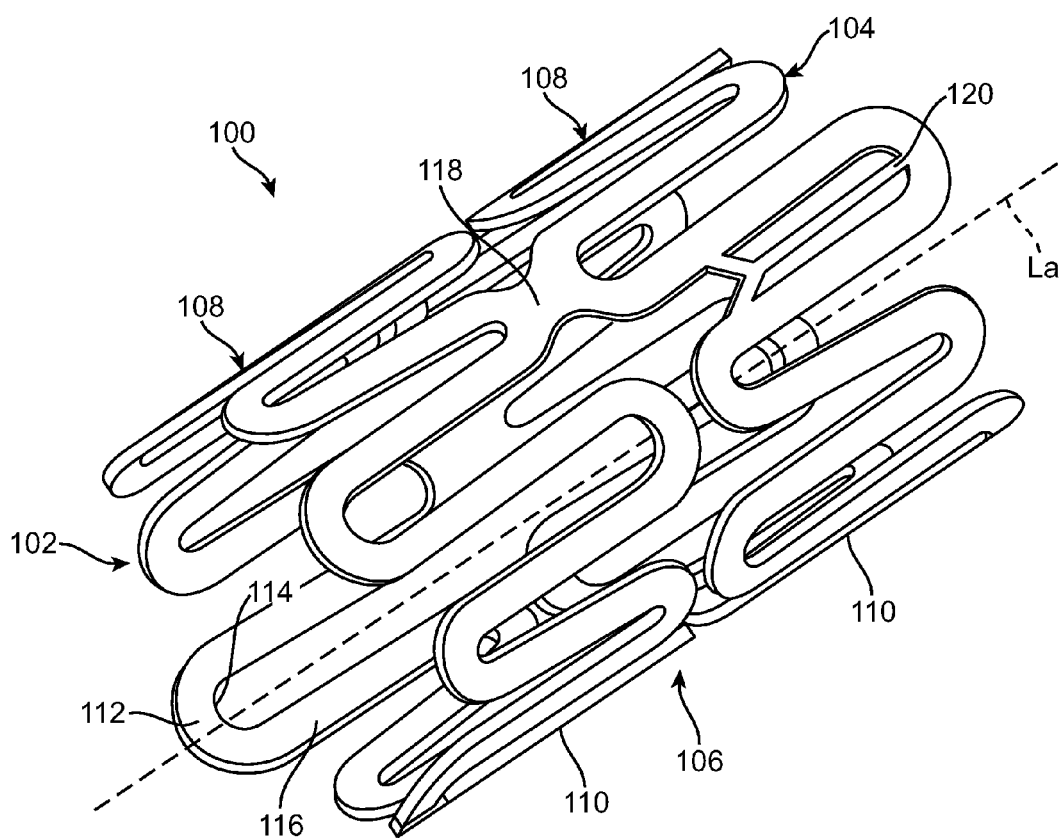
FIG. 1 is a perspective view of an exemplary stent prosthesis configured to fit into a body lumen such as a blood vessel.

FIG. 1 illustrates an example of stent prosthesis 100 configured to fit into a body lumen such as a blood vessel. Stent 100 has a generally tubular or cylindrical expandable body 106 having longitudinal axis $L_a$, a proximal end 102, and a distal end 104. Longitudinal axis $L_a$ extends within cylindrical body 106 from proximal end 102 to distal end 104 of stent 100. A plurality of adjacent radially expandable cylindrical rings 108 are aligned substantially parallel relative to longitudinal axis $L_a$ so as to form the cylindrical tubular shape of stent 100. One of ordinary skill in the art will appreciate that stent 100 can have any number of cylindrical rings 108 depending upon the desired length of stent 100.

Figure 2:
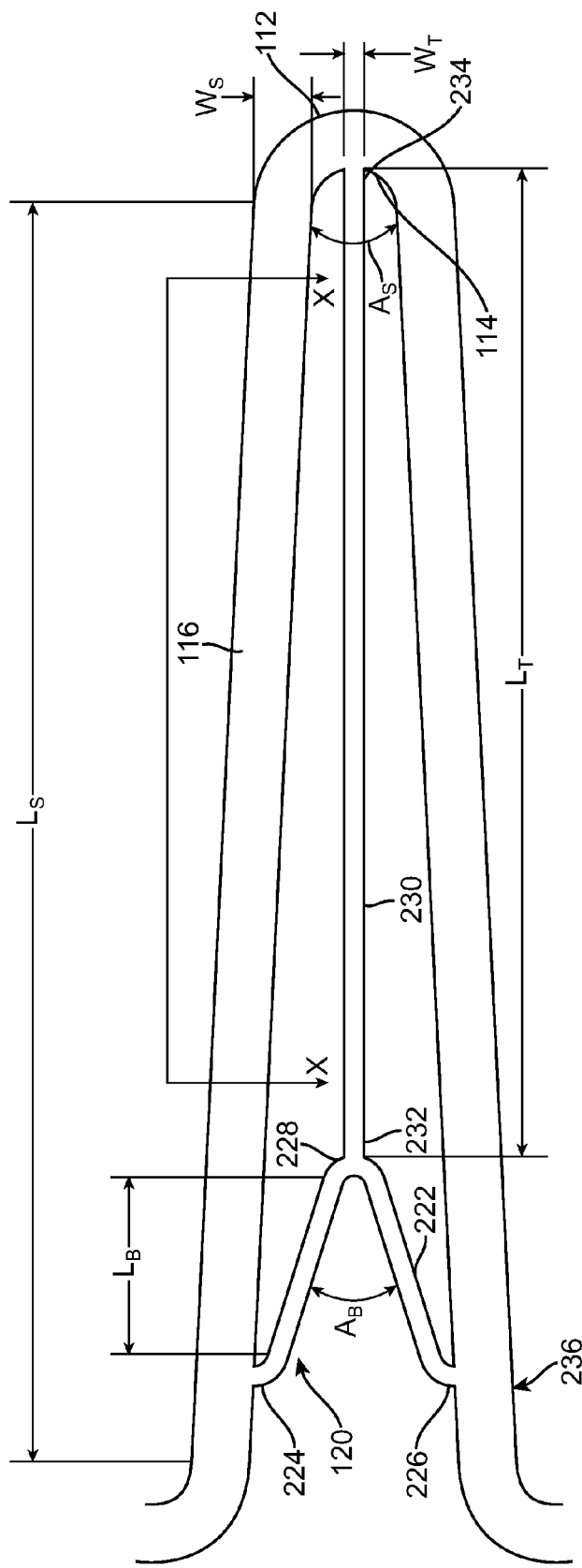
FIG. 2 is a schematic of a portion of a stent strut of FIG. 1 having a Y-shaped member to induce crown flaring, wherein the stent strut is in the unexpanded configuration.

Cylindrical rings 108 are formed from stent struts 110 having a wavelike or sinusoidal pattern of straight segments 116 with crowns 112 (i.e., alternating turns facing opposite longitudinal directions) connecting adjacent straight segments 116. As shown in FIG. 2, straight segments 116 include a length $L_S$ and a width $W_S$, and crowns 112 define an angle $A_S$. Crowns 112 form valleys 114. For purposes of this application, it will be understood that crowns are the concave turns or curves of a wavelike or sinusoidal band and valleys are the open curved or hollowed out portion formed by the crowns of a wavelike or sinusoidal band. Adjacent stent struts 110 are aligned such that a crown of one stent strut is aligned with a corresponding crown of an adjacent stent strut. At least one connection 118 is formed between adjacent stent struts 110 where crowns 112 of adjacent stent struts 110 are aligned. Connections 118 are preferably formed by welding the turns together, such as by resistance welding, friction welding, laser welding or another form of welding such that no additional materials are used to connect stent struts 110. Alternatively, stent struts 110 can be connected by soldering, by the addition of a connecting element between the turns, or by another mechanical method. Further, stent 100 may be formed pre-connected as a unitary structure, such as by laser cutting or etching the entire stent body from a hollow tube or sheet. Other connections or ways to join adjacent struts would be apparent to one skilled in the art and are included herein. Stent 100 includes a Y-shaped member 120 attached to one of the crowns 112 of stent strut 110 to induce flaring of the crown. Y-shaped member 120 will be explained in more detail below with respect to FIG. 2.

Stent 100 may include a valve (not shown) therein capable of blocking flow in one direction to regulate flow there through. The valve would be sealingly and permanently attached to the interior surface of the stent and/or graft material enclosing or lining the stent. The graft material may be a low-porosity woven fabric, such as polyester, Dacron fabric, or PTFE, which creates a one-way fluid passage when attached to the stent. The valve may be a bovine or porcine valve treated and prepared for use in a human, or may be a mechanical valve or a synthetic leaflet valve. For example, a percutaneously implanted bovine or porcine valve treated and prepared for use in a human may be sewn inside a laser-welded stent such as that described in U.S. Pat. No. 5,957,949 titled "Percutaneous Placement Valve Stent" to Leonhardt et al., the contents of which are incorporated by reference herein in its entirety.

Stent 100 has an unexpanded configuration sufficient for delivery to the treatment site and an expanded or deployed configuration in which stent 100 comes into contact with the vessel wall. Stent 100 may be expanded in several ways. In one embodiment which will be explained in more detail herein, stent 100 may be balloon-expandable. Stent 100 may be collapsed to a contracted or compressed configuration on top of a balloon of a balloon dilation catheter for delivery to a treatment site, such as the type of balloon used in an angioplasty procedure. As the balloon expands, it physically forces stent 100 to radially expand such that the outside surface of stent 100 comes into contact with the lumen wall. The balloon is then collapsed leaving stent 100 in the expanded or deployed configuration.

Referring now to FIG. 2, embodiments of the present invention relate to the attachment of Y-shaped member 120 to a crown 112. The Y-shaped member 120 is configured to cause the crown 112 to flare outwardly at an angle from the cylindrical stent body when the stent is expanded. Y-shaped member 120 has a V-shaped base 222 and a tether 230. V-shaped base 222 defines an angle $A_B$ and includes a first end 224, a second end 226, an apex 228, a first segment extending between first end 224 and apex 228, and a second segment extending between second end 226 and apex 228. Each segment of V-shaped base 222 has a length $L_B$. Tether 230 has a width $W_T$ and a length $L_T$ and extends between a first end 232 and a second end 234. First end 232 of tether 230 is connected to apex 228 of V-shaped base 222, and second end 234 of tether 230 is connected to valley 114 within crown 112. First and second ends 224, 226 of V-shaped base 222 are connected to straight segments 116, which are connected to crown 112. Thus, as shown in FIG. 2, Y-shaped member 120 is substantially centered within crown 112 and adjacent straight segments 116 that extend therefrom.

FIG. 2 shows crown 112 in an unexpanded or non-flared configuration 236. When stent 100 is in the unexpanded configuration sufficient for delivery to the treatment site, crown 112 in non-flared configuration 236 is approximately parallel with longitudinal axis $L_a$ such that stent 100 has a substantially cylindrical outer surface with a consistent outer diameter. Upon expansion of stent 100, crown 112 flares or curves outwardly from the remainder of the cylindrical stent body so that it protrudes into the vessel wall and creates an anchor that aids fixing stent 100 within the vessel. When flared, crown 112 is angled with respect to longitudinal axis $L_a$ and radially flares at an acute angle from the outer surface of the remainder of the stent body.

Figure 8:
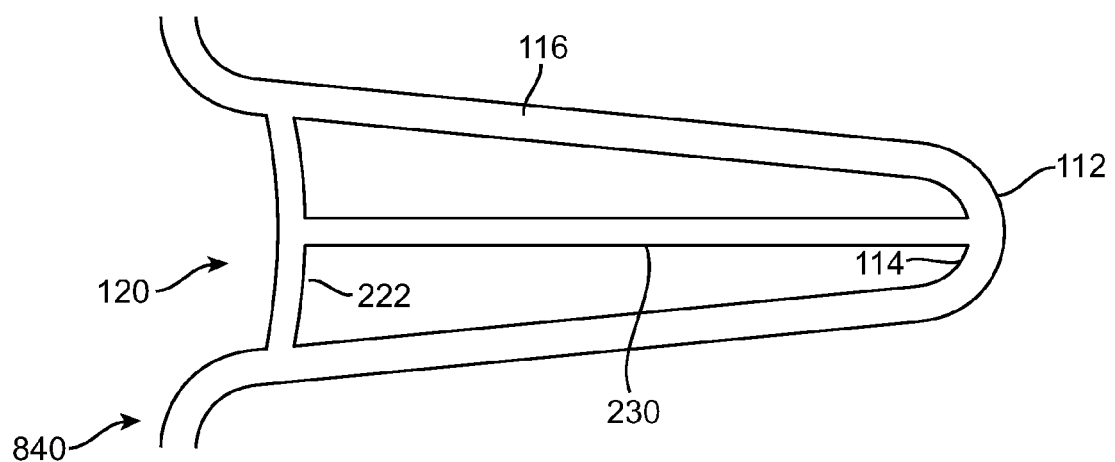
FIG. 8 is a schematic of a portion of a stent strut having a Y-shaped member to induce crown flaring, wherein the stent strut is in the expanded configuration according to an embodiment of the present invention.

The relationship between geometry of Y-shaped member 120 and the geometry of stent strut 110 determines the amount or degree of flare. More particularly, as stent 100 is expanded, angle $A_S$ of crown 112 and angle $A_B$ of V-shaped base 222 are increased. By design, the geometry of V-shaped base 222 leads to a more rapid increase in the angle $A_B$ as compared to the increase of angle $A_S$ of crown 112, and therefore leads to a disparity between the foreshortening of V-shaped base 222 and crown 112. Stated another way, since length $L_B$ of V-shaped base 222 is considerably shorter than length $L_S$ of straight segment 116, a greater angular change occurs at apex 228 of V-shaped base 222 than at crown 112 during deployment. The greater foreshortening rate of V-shaped base 222 imparts a tensile force to the inside curve of crown 112 via tether 230 to pull crown 112 both radially and axially, which results in the desired flaring behavior. The greater the ratio between $L_S$ to $L_B$, the greater the difference in the respective foreshortening of the V-shaped base 222 and crown 112, and therefore the greater the resulting flare effect. During expansion, angle $A_B$ of V-shaped base 222 may approach 180 degrees such that Y-shaped member 120 transforms to a T-shape as shown in FIG. 8.

Figure 3:
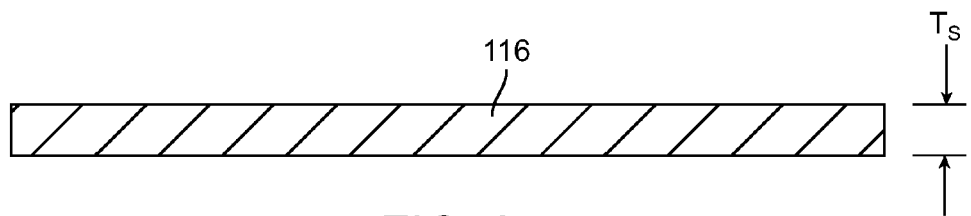
FIG. 3 is a partial sectional view taken along line X-X of FIG. 2 according to one embodiment of the present invention.
Figure 3A:
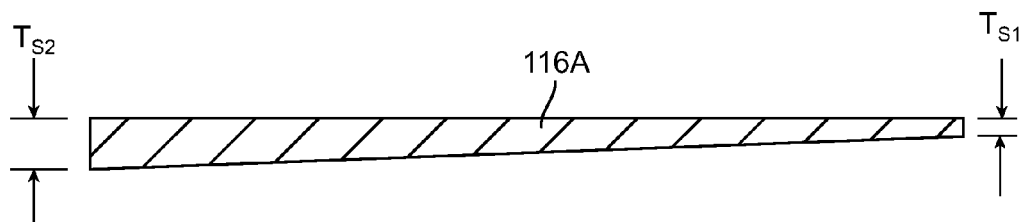
FIG. 3A is a partial sectional view similar to that of FIG. 3 according to another embodiment of the present invention.
Figure 3B:
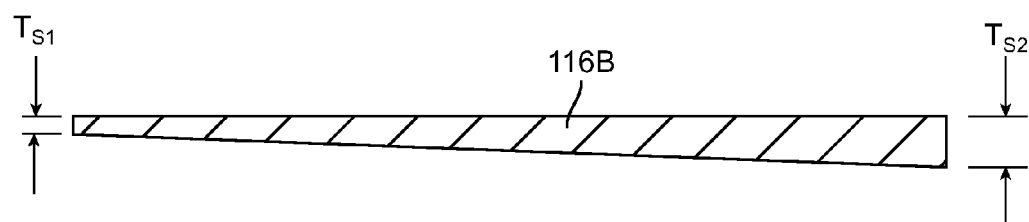
FIG. 3B is a partial sectional view similar to that of FIG. 3 according to another embodiment of the present invention.

Further, the cross-sectional thickness of stent strut 110 can influence the amount of flare. More particularly, FIG. 3 illustrates a sectional view along line X-X of FIG. 2. As shown, straight segment 116 of stent strut 110 has a thickness $T_S$. Thickness $T_S$ may significantly influence the amount of allowed flaring because relatively thicker dimensions will not allow for a substantial amount of outward bending of segment 116 and thus result in a relatively smaller amount of flare, while relatively thinner dimensions will allow for a substantial amount of outward bending of segment 116 and thus result in a relatively greater amount of flare. Thickness $T_S$ may be constant along the length of segment 116 as shown in FIG. 3. In an alternative embodiment, thickness $T_S$ may vary along the length of segment 116. As shown in FIG. 3A, straight segment 116A may have a first end of a relatively thicker dimension $T_{S2}$ and a second end of a relatively thinner dimension $T_{S1}$. Straight segment 116A gradually becomes thinner as it approaches crown 112 to allow for a greater amount of flare of crown 112. In another embodiment, it may be desirable to vary the thickness of the stent strut to restrict the amount of flare. For example, as shown in FIG. 3B, straight segment 116B may have a first end of a relatively thinner dimension $T_{S1}$ and a second end of a relatively thicker dimension $T_{S2}$. Straight segment 116B gradually becomes thicker as it approaches crown 112 to allow for a smaller amount of flare of crown 112.

Figure 4:
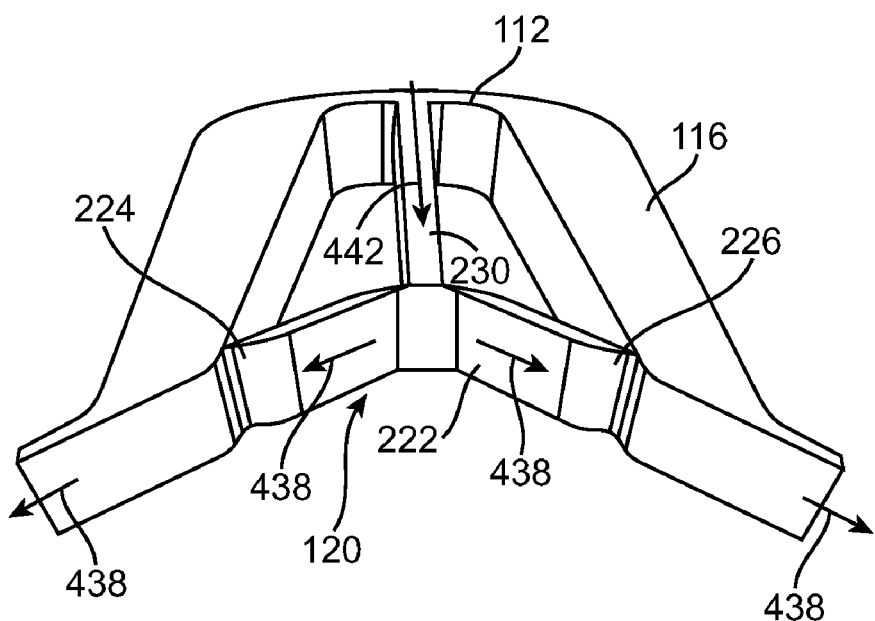
FIG. 4 is an isometric schematic of force vectors imparted to a portion of a stent strut during deployment.
Figure 5:
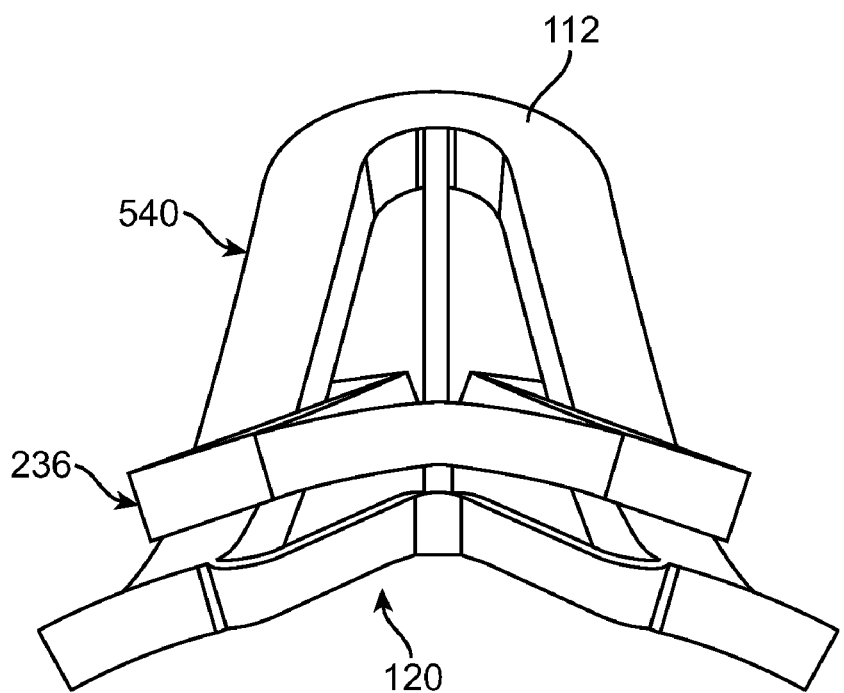
FIG. 5 is an isometric schematic of a portion of a stent strut transforming between a non-flared configuration and a flared configuration during stent deployment.
Figure 6:
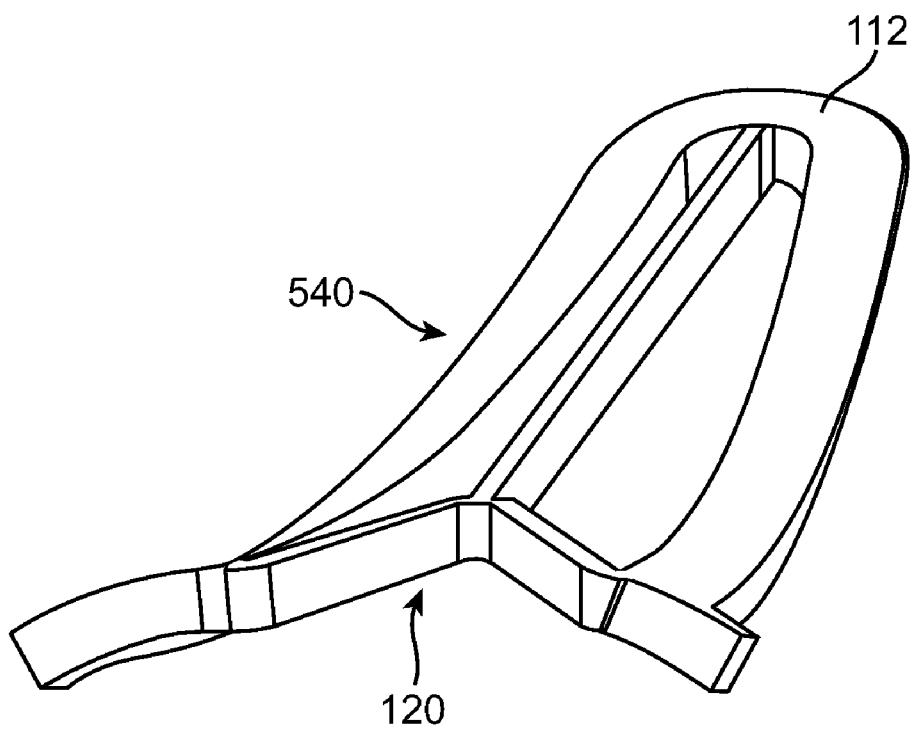
FIGS. 6-7 are isometric views of the stent strut portion of FIG. 5 in the flared configuration.
Figure 7:
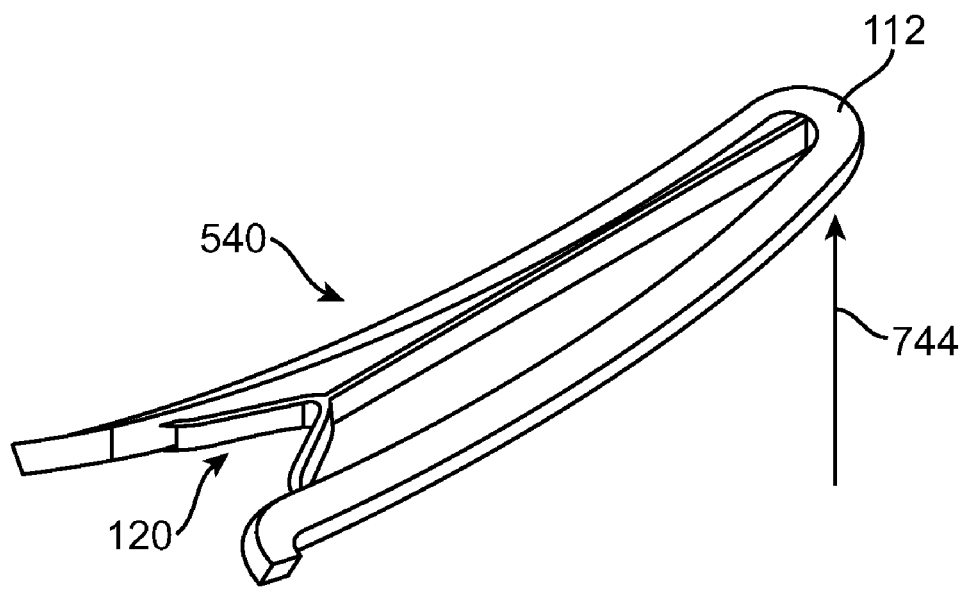

FIGS. 4-5 are schematic illustrations of the force vectors imparted to a portion of a stent having a Y-shaped member attached thereto during deployment. Referring to FIG. 4, when stent 100 radially expands, first and second ends 224, 226 of V-shaped base 222 move away from each other as indicated by directional arrows 438. Thus, the distance between first end 224 and second end 226 of V-shaped base 222 increases upon expansion of stent 100, causing shortening of Y-shaped member 120 as indicated by the directional arrow 442. This forced shortening causes tether 230 to apply longitudinal tension on crown 112 such that crown 112 lifts or projects outwardly from the outer surface of the cylindrical stent body as indicated by directional arrow 744 shown in FIG. 7. It will be understood that in order to allow crown 112 to flare, crown 112 of stent strut 110 is not connected to an adjacent stent strut 110. Since crown 112 is "free" or unconnected, crown 112 is allowed to be lifted or flared due to the expansion of Y-shaped member 120. As shown in FIG. 5, crown 112 transforms from non-flared configuration 236 to a flared configuration 540 during stent deployment. Crown 112 in the flared configuration is also shown in the isometric views of FIGS. 6-7. In flared configuration 540, crown 112 is configured to protrude into the vessel wall and creates an anchor that aids fixing stent 100 within the vessel.

Y-shaped member 120 may be attached to any crown 112 that is to be flared upon expansion. In one embodiment, the outermost crowns at the proximal and/or distal ends of the stent may be flared in order to prevent stent migration, particularly when the stent is seated within an ostium of a vessel. Flow through a "straight" stent is primarily directed straight through. However, due to the relatively smaller inlet of a "straight" stent, some of the flow "misses" the inlet and swirls/rolls off the sides of the proximal end of the stent. Similarly, due to the relatively smaller outlet of a "straight" stent, some of the flow reverses and swirls/rolls off the sides of the distal end of the stent. Such swirling/rolling flow may cause unwanted rotational migration of the stent, as well as a phenomenon known as "watermelon seeding" which causes the stent to migrate distally an unpredictable distance. In comparison, a stent having flared ends may avoid such unwanted migration, as well as prevent hemostasis and subsequent thrombogenic effects. Due to the relatively larger inlet of a flared inlet end, the flow is directed straight through the proximal end of the stent without some of the flow missing the inlet. Similarly, due to the relatively larger outlet of a flared outlet end, the flow is directed straight out of the distal end of the stent without some of the flow reversing back towards the stent.

Figure 9:
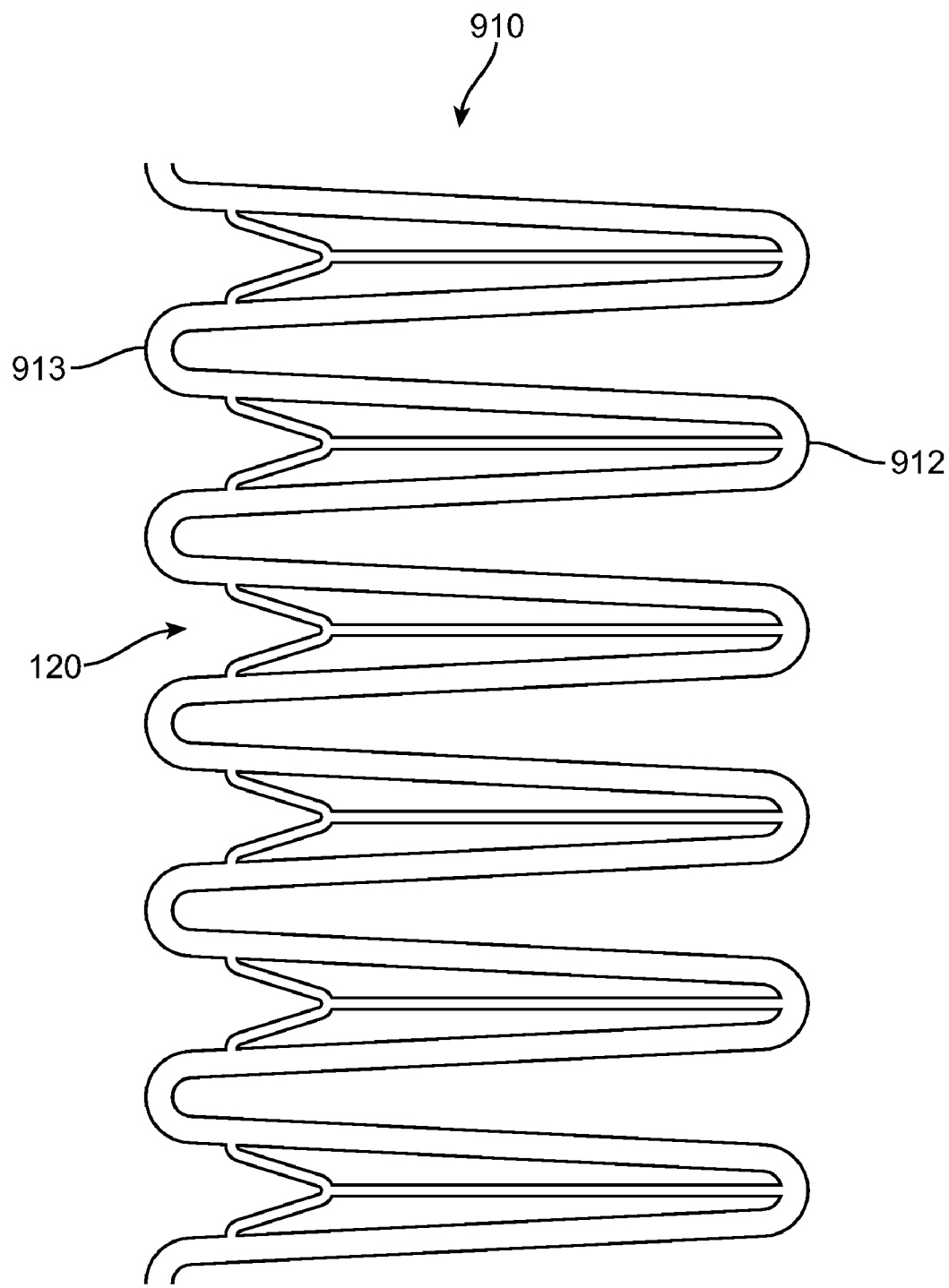
FIG. 9 is a schematic of a stent strut having multiple Y-shaped members to induce crown flaring of the outermost crowns.
Figure 10A:
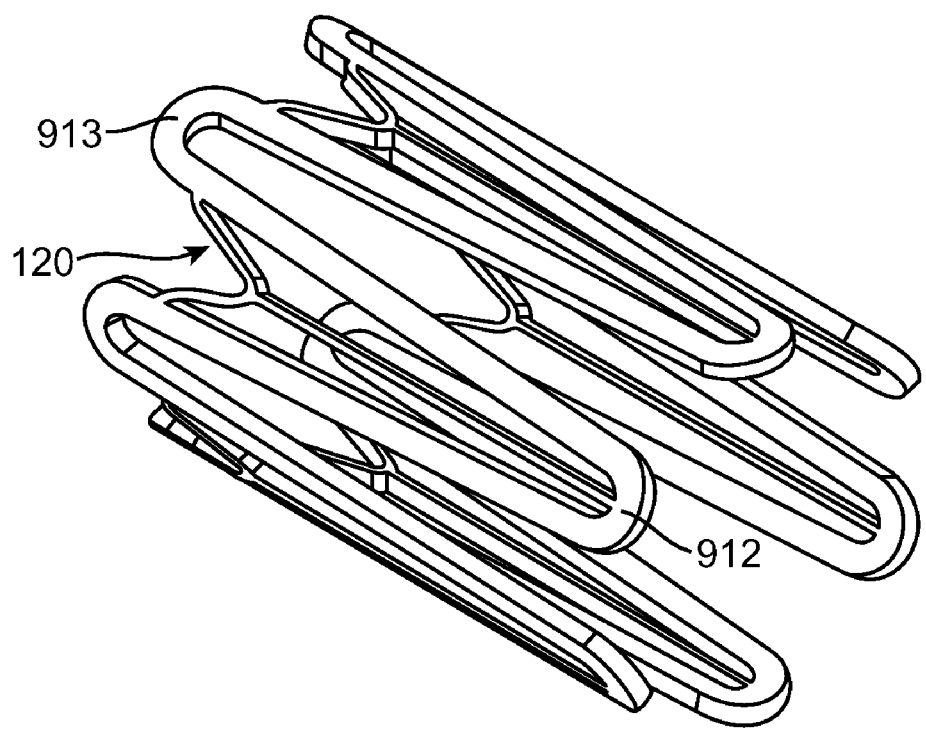
FIG. 10A-10B are isometric and front views of the stent strut of FIG. 4 formed into a cylindrical ring, wherein the stent strut is in an unexpanded configuration.
Figure 10B:
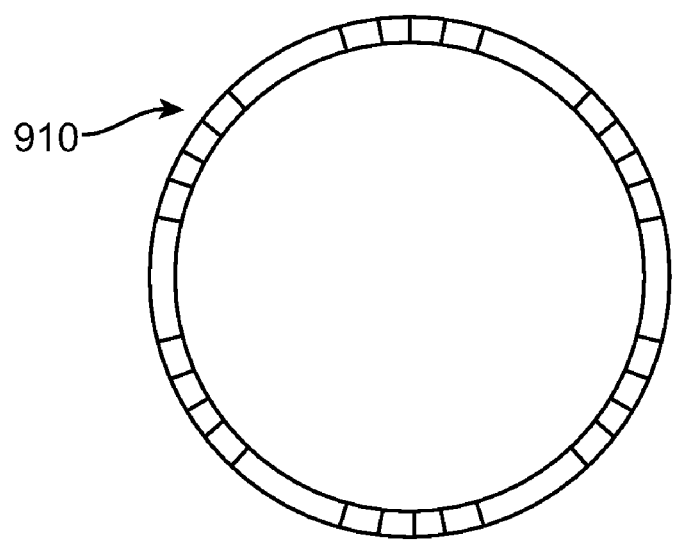
Figure 11A:
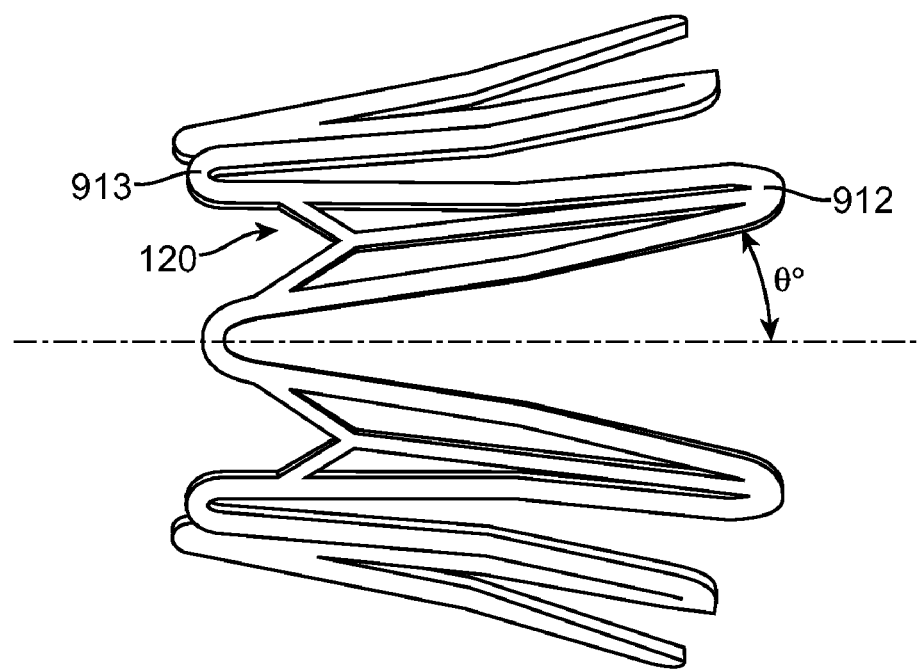
FIG. 11A-11B are side and front views of the stent strut of FIG. 4 formed into a cylindrical ring, wherein the stent strut is in an expanded configuration.
Figure 11B:
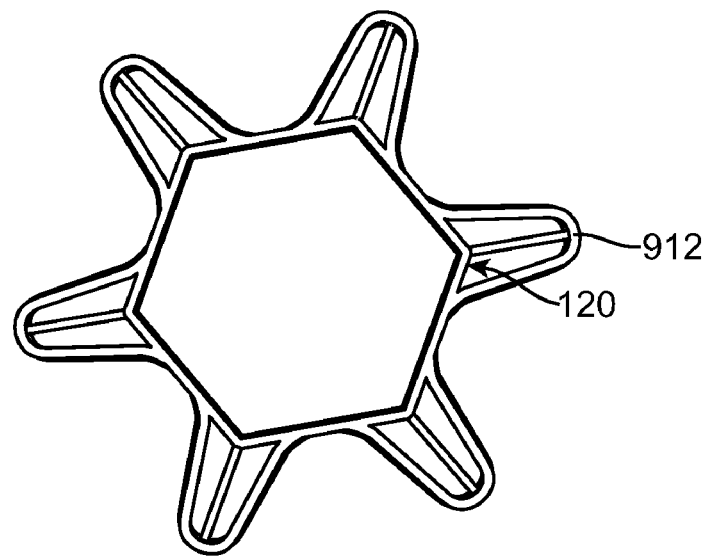

FIGS. 9, 10A, 10B, 11A, and 11B illustrate one embodiment of the present invention in which all of the outermost crowns 912 of a stent strut 910 includes a Y-shaped member 120 such the outermost crowns 912 flare upon expansion. FIG. 9 is a schematic of stent strut 910 laid out flat, while FIGS. 10A-10B are side and front views of stent strut 910 of FIG. 9 formed into a cylindrical ring in the unexpanded configuration. FIGS. 11A-11B are side and front views of stent strut 910 formed into a cylindrical ring in the expanded configuration. This embodiment may be utilized at the proximal and/or distal ends of a stent such that the end(s) of the stent flare in order to prevent stent migration as described above.

Although not shown, one or more of the non-flared inner crowns 913 of stent strut 110 would be connected to the remainder of the body of the stent. As shown in FIGS. 11A-11B, upon expansion of the stent, outermost crowns 912 flares outwardly at an acute angle Ø with respect to longitudinal axis $L_a$ to create an anchor that aids fixing or retaining the stent within the vessel. For example, flaring of outermost crowns 912 may assist in seating the stent within an ostium of a bifurcated vessel. Angle Ø may range between zero and ninety degrees. In one embodiment depicted in FIGS. 11A-11B, angle Ø is approximately forty-five degrees. The outer diameter of the outermost flared crowns 912 is greater than the outer diameter of non-flared inner crowns 912 of stent strut 910.

Figure 12:
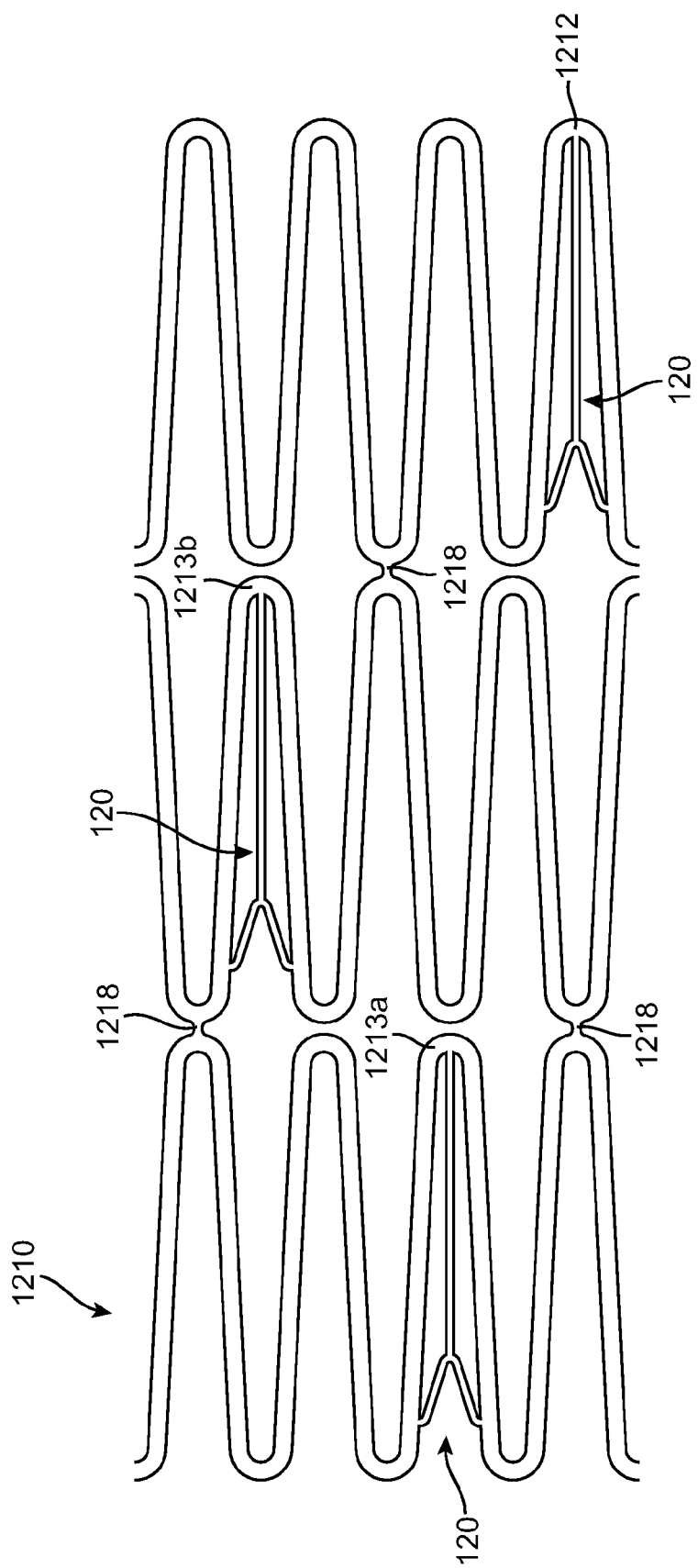
FIG. 12 is a schematic of multiple stent struts having Y-shaped members to induce crown flaring of select crowns.

As previously mentioned, Y-shaped member 120 may be added to any crown that is to be flared upon expansion. In another embodiment of the present invention shown in FIG. 12, Y-shaped members 120 may be added in a "random" or "staggered" pattern so that the flared crowns act as barbs along the cylindrical stent body when the stent is expanded within the vessel. FIG. 12 is a schematic of multiple stent struts 1210 connected at connections 1218. As shown, some free or unconnected interior crowns 1213a, 1213b located between the proximal end and the distal end of the stent include Y-shaped members 120 to induce flaring thereof upon expansion of the stent. The crowns to be flared also include an outermost crown 1212. Upon expansion of the stent, crowns 1212, 1213a, 1213b having Y-shaped members 120 flare so that they protrude into the vessel wall and create an anchor that aids fixing the stent within the vessel.

Preferably, the stent of the present invention is crimped onto a conventional balloon dilation catheter for delivery to a treatment site and expanded by the radial force of the balloon. Conventional balloon catheters that may be used in the present invention include any type of catheter known in the art, including over-the-wire catheters, rapid-exchange catheters, core wire catheters, and any other appropriate balloon catheters. For example, conventional balloon catheters such as those shown or described in U.S. Pat. Nos. 6,736,827; 6,554,795; 6,500,147; and 5,458,639, which are incorporated by reference herein in their entirety, may be used in conjunction with stent 100 of the present invention.

Figure 13:
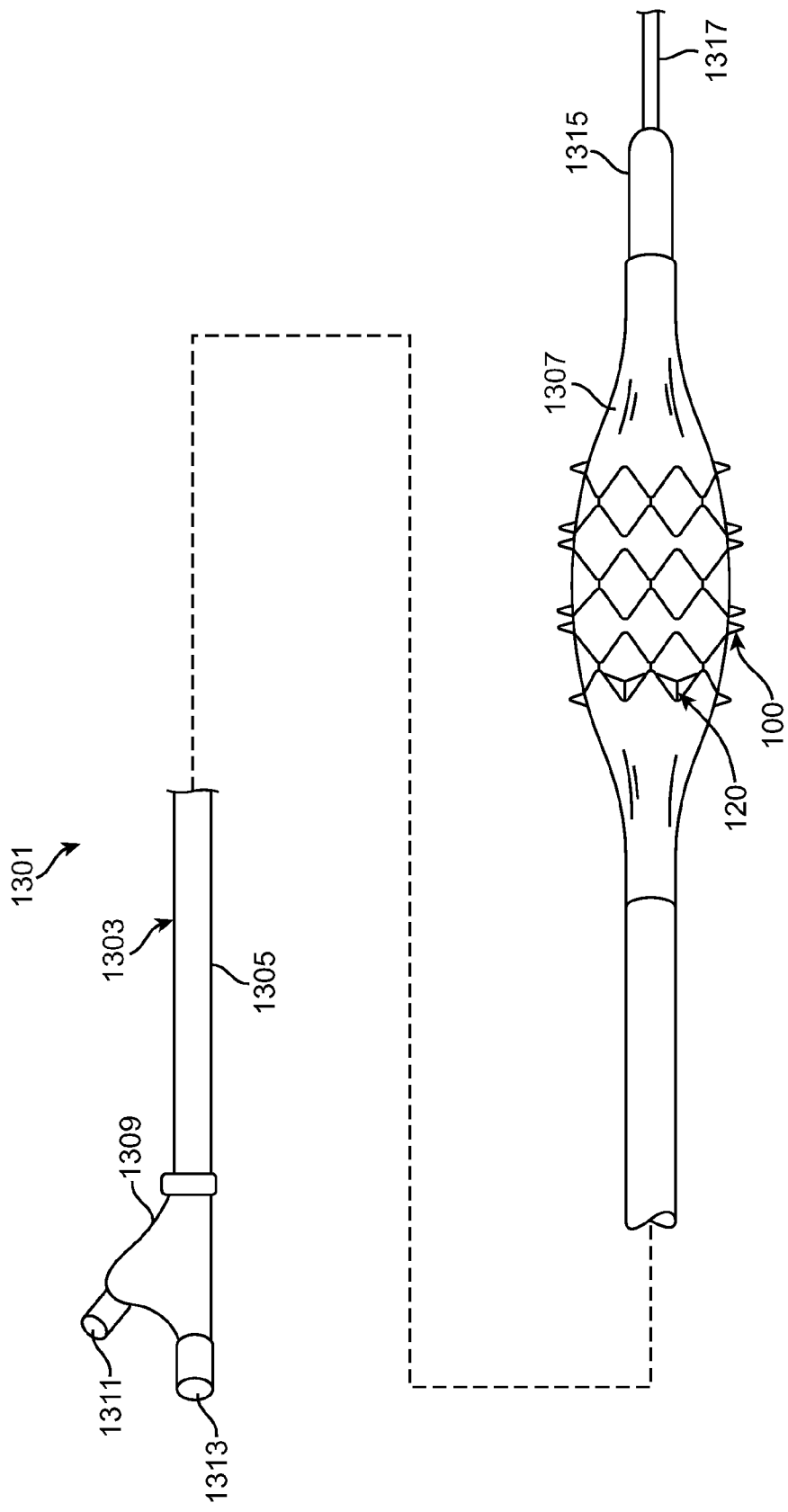
FIG. 13 is a side elevational view of a stent delivery system in accordance with an embodiment of the present invention.

FIG. 13 is an illustration of a stent delivery system 1301 for tracking stent 100 to a target site in accordance with an embodiment of the present invention. Stent delivery system 1301 includes an over-the-wire catheter 1303 having a proximal shaft 1305, a guidewire shaft 1315, and a balloon 1307. Proximal shaft 1305 has a proximal end attached to a hub 1309 and a distal end attached to a proximal end of balloon 1307. Guidewire shaft 1315 extends between hub 1309 and a distal tip of catheter 1303 through proximal shaft 1305 and balloon 1307. Hub 1309 includes an inflation port 1311 for coupling to a source of inflation fluid. Inflation port 1311 fluidly communicates with balloon 1307 via an inflation lumen (not shown) that extends through proximal shaft 1305. In addition, hub 1309 includes a guidewire port 1313 that communicates with a guidewire lumen (not shown) of guidewire shaft 1315 for receiving a guidewire 1317 there through. As described herein, guidewire shaft 1315 extends the entire length of catheter 1303 in an over-the-wire configuration. However, as would be understood by one of ordinary skill in the art, guidewire shaft 1315 may alternately extend only within the distal portion of catheter 1303 in a rapid-exchange configuration. A stent 100 including at least one Y-shaped member 120 formed in accordance with an embodiment of the present invention is positioned over balloon 1307. If desired, a sheath (not shown) may be provided to surround stent 100 to facilitate tracking of the stent delivery system 1301 over guidewire 1317 through the vasculature to a site of a stenotic lesion.

Deployment of balloon expandable stent 100 is accomplished by threading catheter 1303 through the vascular system of the patient until stent 100 is located within target tissue, for example, a lesion which may include plaque obstructing the flow of blood through the vessel. Once positioned, a source of inflation fluid is connected to inflation port 1311 of hub 1309 so that balloon 1307 may be inflated to expand stent 100 as is known to one of ordinary skill in the art. Balloon 1307 of catheter 1303 is inflated to an extent such that stent 100 is expanded or deployed against the vascular wall of the vessel to maintain the opening. Crowns 112 having Y-shaped members 120 will flare upon expansion and protrude into the vessel wall to anchor stent 100 within the vessel. Stent deployment can be performed following treatments such as angioplasty, or during initial balloon dilation of the treatment site, which is referred to as primary stenting.

However, rather than being balloon-expandable as described above, one of ordinary skill in the art can appreciate that stent 100 of the present invention can be adapted for any type of delivery method. For example, in another embodiment of the present invention, stent 100 may be self-expanding. Deployment of stent 100 may be facilitated by utilizing shape memory characteristics of a material such as nickel-titanium (nitinol). More particularly, shape memory metals are a group of metallic compositions that have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. This enables the stent to be inserted into the body in a deformed, smaller state so that it assumes its "remembered" larger shape once it is exposed to a higher temperature, i.e., body temperature or heated fluid, in vivo. Thus, self-expanding stent 100 can have two states of size or shape, a contracted or compressed configuration sufficient for delivery to the treatment site and a deployed or expanded configuration having a generally cylindrical shape for contacting the vessel wall, wherein crowns 112 having Y-shaped members 120 will flare upon expansion of stent 100 and protrude into the vessel wall to anchor stent 100 within the vessel.

In another embodiment in which stent 100 is self-expanding, body portion 106 may be constructed out of a spring-type or superelastic material such as nickel-titanium (nitinol). A sheath (not shown) may be provided to surround and contain stent 100 in a contracted or compressed position. Once stent 100 is in position within the target vessel, the sheath may be retracted, thus releasing stent 100 to assume its expanded or deployed configuration. Crowns 112 having Y-shaped member 120 will flare upon expansion of stent 100 and protrude into the vessel wall to anchor stent 100 within the vessel.

Stent struts 110 of stent 100 may be made from a variety of medical implantable materials, including, but not limited to, stainless steel, nickel-titanium (nitinol), cobalt-chromium, tantalum, ceramic, nickel, titanium, aluminum, polymeric materials, nickel-cobalt alloy such as MP35N, titanium ASTM F63-83 Grade 1, niobium, platinum, gold, silver, palladium, iridium, combinations of the above, and the like. One widely used material for stents is stainless steel, particularly 316L stainless steel, which is particularly corrosion resistant. Once implanted, the metallic stent struts provides artificial radial support to the wall tissue.

Y-shaped member 120 may be made from the same or a different material from stent strut 110. In one embodiment, stent struts 110 and Y-shaped members 120 may be both formed from a plastically deformable material such as stainless steel that is expandable by the radial force of a balloon of a balloon dilation catheter. In another embodiment, stent struts 110 may be made from a plastically deformable material such as stainless steel that is expandable by the radial force of a balloon of a balloon dilation catheter while Y-shaped members 120 are formed from an elastically deformable material such as nickel-titanium (nitinol) or another shape memory or superelastic material. Forming Y-shaped members 120 from a superelastic material may assist in the expansion of Y-shaped members 120 to induce flaring of crowns. In yet another embodiment, it may be desirable to form Y-shaped member 120 from a bioabsorbable and/or biodegradable material that is selected to absorb or degrade in vivo over time. Bioabsorbable/biodegradable materials include magnesium or a magnesium alloy, other bioabsorbable metals, or bioabsorbable polymers such as polyactic acid, polyglycolic acid, collagen, polycaprolactone, hylauric acid, co-polymers of these materials, as well as composites and combinations thereof. Bioabsorbable Y-shaped members hold crowns of the stent in the flared configuration for a sufficient time to allow for endothelialization of the flared crowns of the stent strut. The term "endothelialization" is meant to describe the process in which a foreign object, such as the stent strut in embodiments of the present invention, becomes incorporated into the walls of the lumen by tissue ingrowth or encapsulation.

Stent 100 may not always be visible to a physician viewing, for example, an X-ray fluoroscopy device while deploying and/or positioning stent 100 into the vessel. Although not required, portions of the stent may be selectively plated with platinum or other biocompatible material to provide improved visibility during fluoroscopy. In one embodiment of the present invention, one or more radiopaque markers (not shown) may be attached to stent 100 at one or more predetermined locations. The marker may be formed of platinum or any other relatively heavy metal, which may be generally visible by X-ray fluoroscopy. For example, the marker may be attached to proximal end 102 or distal end 104 of stent 100 to allow a relatively high degree of accuracy for positioning stent 100 into the vessel.

In one embodiment of the present invention, at least a portion of stent 100 may be coated with a therapeutic agent (not shown). Stent 100 may be coated with a controlled-release polymer and/or drug, as known in the art, for reducing the probability of undesired side effects, e.g., restenosis. The therapeutic agent can be of the type that dissolves plaque material forming the stenosis or can be such as an antineoplastic agent, an antiproliferative agent, an antibiotic, an antithrombogenic agent, an anticoagulant, an antiplatelet agent, an anti-inflammatory agent, combinations of the above, and the like. Such drugs can include TPA, heparin, urokinase, or sirolimus, for example. Of course stent 100 can be used for delivering any suitable medications to the walls of a body vessel.

Stent struts 110 having select Y-shaped members 120 may be laser cut from stainless steel tubing, or any other appropriate tubing, having an outer diameter of approximately 0.25 inches and a wall thickness of approximately 0.012 inches. In this manner, the plurality of stent struts 110 having Y-shaped members 120 at crown locations may be formed connected together such that the stent body is a unitary structure. Alternatively, stent struts 110 may be laser cut from stainless steel tubing, or any other appropriate tubing, and Y-shaped members may be formed separately and attached to crowns 112 of stent struts 110. Y-shaped members may be attached via any suitable mechanical method, including welding, soldering, or by another mechanical method.

In addition, rather than being laser cut from any appropriate tubing material, stent 100 may be formed using any of a number of different methods that would be apparent to one skilled in the art. For example, stent struts 110 may be formed by winding a wire or ribbon around a mandrel to form a strut pattern like those described above and then welding or otherwise mechanically connecting two ends thereof to form a cylindrical ring 108. A plurality of cylindrical rings 108 formed in this manner are subsequently connected together to form the longitudinal tubular body of stent 100. Y-shaped members 120 may be formed separately and attached to crowns 112 of stent struts 110. Alternatively, stent struts 110 may be manufactured by machining tubing or solid stock material into toroid bands, and then bending the bands on a mandrel to form the pattern described above. Again, a plurality of cylindrical rings 108 formed in this manner are subsequently connected together to form the longitudinal tubular body of stent 100. Y-shaped members 120 may be formed separately and attached to one or more crowns 112 of stent struts 110. Chemical etching or another method of cutting a desired shape out of a solid stock material or tubing may also be used to form stent 100 of the present invention. In this manner, the plurality of stent struts 110 having Y-shaped members 120 may be formed connected together such that the stent body is a unitary structure. Further, stent 100 of the present invention may be manufactured in any other method that would be apparent to one skilled in the art. The cross-sectional shape of stent 100 may be circular, ellipsoidal, rectangular, hexagonal rectangular, square, or other polygon, although at present it is believed that circular or ellipsoidal may be preferable.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent for use within a body lumen, the stent comprising:

a stent strut having a sinusoidal pattern of straight segments and crowns, wherein all of the crowns of the stent strut are approximately parallel with a longitudinal axis of the stent when the stent is in an unexpanded configuration for delivery within the body lumen; and a Y-shaped member attached to at least one crown of the stent strut such that the Y-shaped member is substantially centered within the at least one crown and first and second straight segments attached to the at least one crown, wherein the Y-shaped member includes a V-shaped base and a tether, the V-shaped base having a first end directly connected to the first straight segment, a second end directly connected to the second straight segment and an apex attached to the tether such that the tether extends between the apex of the V-shaped base and a valley formed by the at least one crown, wherein when the stent is in an expanded configuration for contacting a vessel wall of the body lumen the at least one crown having the Y-shaped member attached thereto radially flares outward from an outer surface of the stent such that the at least one crown is at an acute angle with respect to the longitudinal axis of the stent.

2. The stent of claim 1, wherein the at least one crown forms approximately a forty-five degree angle with respect to the longitudinal axis of the stent when the stent is in the expanded configuration.

3. The stent of claim 1, wherein the stent includes a plurality of stent struts formed into a plurality of radially expandable cylindrical rings aligned substantially parallel to the longitudinal axis so as to form a cylindrically-shaped tubular body.

4. The stent of claim 3, wherein the plurality of radially expandable cylindrical rings are aligned such that crowns of adjacent stent struts are aligned and at least one connection is formed between aligned crowns of adjacent stent struts.

5. The stent of claim 4, wherein the at least one crown is not connected to a crown of an adjacent stent strut.

6. The stent of claim 1, wherein the Y-shaped member approaches a T-shape when the stent is in the expanded configuration.

7. The stent of claim 6, wherein the tether applies longitudinal tension to the at least one crown such that the at least one crown lifts or projects outwardly from an outer surface of the stent when the stent is in the expanded configuration.

8. The stent of claim 1, wherein the at least one crown is an outermost crown located at a proximal end or a distal end of the stent.

9. The stent of claim 1, wherein the at least one crown is an interior crown located between a proximal end and a distal end of the stent.

10. The stent of claim 1, wherein the stent strut has a thickness that is constant along the length of the straight segment.

11. The stent of claim 1, wherein the stent strut has a thickness that varies along the length of the straight segment.

* * * * *